United States Patent
Köhler et al.

(10) Patent No.: US 7,344,895 B2
(45) Date of Patent: Mar. 18, 2008

(54) PRODUCTION AND USE OF IN SITU-MODIFIED NANOPARTICLES

(75) Inventors: Burkhard Köhler, Leverkusen (DE); Kerstin Bohmann, Köln (DE); Werner Hoheisel, Köln (DE); Markus Haase, Hamburg (DE); Stefan Haubold, Hamburg (DE); Christiane Meyer, Hamburg (DE); Thorsten Heidelberg, Hamburg (DE)

(73) Assignee: Bayer Technology Services GmbH, Leverkusen (DE)

( * ) Notice: Subject to any disclaimer, the term of this patent is extended or adjusted under 35 U.S.C. 154(b) by 0 days.

(21) Appl. No.: 10/540,168

(22) PCT Filed: Dec. 6, 2003

(86) PCT No.: PCT/EP03/13816

§ 371 (c)(1),
(2), (4) Date: Aug. 29, 2005

(87) PCT Pub. No.: WO2004/058914

PCT Pub. Date: Jul. 15, 2004

(65) Prior Publication Data

US 2006/0063155 A1  Mar. 23, 2006

(30) Foreign Application Priority Data

Dec. 20, 2002  (DE)  ............................ 102 59 935

(51) Int. Cl.
*G01N 33/543* (2006.01)
*G01N 37/00* (2006.01)
*G01N 33/24* (2006.01)

(52) U.S. Cl. ..................... 436/523; 436/525; 436/56; 436/80; 436/81; 436/82; 977/810; 977/811; 530/405

(58) Field of Classification Search ............... 436/523, 436/525, 56, 80, 81, 82; 977/810, 811; 530/405
See application file for complete search history.

(56) References Cited

U.S. PATENT DOCUMENTS

2003/0032192 A1* 2/2003 Haubold et al. ............. 436/56
2004/0014060 A1* 1/2004 Hoheisel et al. ............. 435/6

FOREIGN PATENT DOCUMENTS

EP  0 672 673 A  9/1995
WO  WO 02/20696  3/2002

OTHER PUBLICATIONS

ANON; "Derivaties of aminomethylphosphonic acid"; Research Disclosure (1979); p. 177; XP002277288.

* cited by examiner

*Primary Examiner*—Long V. Le
*Assistant Examiner*—Shafiqul Haq
(74) *Attorney, Agent, or Firm*—Norris, McLaughlin & Marcus PA

(57) ABSTRACT

A process for synthesizing nanoparticles, in particular metal salt nanoparticles. To the synthesis mixture is added a modifying reagent which binds, by means of a first functional group, to the nanoparticle surface and which carries a second functional group for binding to molecules which are specifically selected in dependence on the subsequent use of the nanoparticles. This dispenses with a postsynthetic, separate, application-specific modification step. A new substance class, the pentaalkyl iminobis(methylenephosphono)carboxylates, are particularly suitable for this purpose. These modifying reagents permit the nanoparticles to grow in a specifically controlled manner and, at the same time, modify the surface of the growing nanoparticles, (in-situ) during the synthesis, such that the particles can be very readily dissolved in a large number of solvents and carry functional groups for coupling on molecules, resulting in the particles having, immediately after having been synthesized, a certain all-round usability.

11 Claims, 1 Drawing Sheet

PRODUCTION AND USE OF IN SITU-MODIFIED NANOPARTICLES

Figure 1:
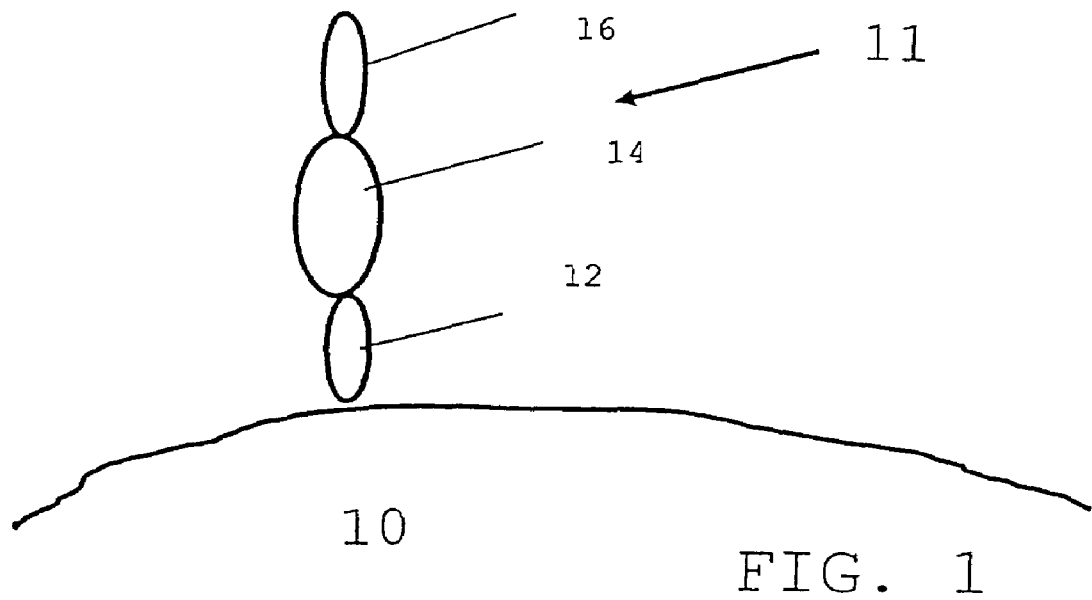

This application is a 371 of PCT/EP2003/013816, filed Dec. 6, 2003, which claims foreign priority benefit under 35 U.S.C. § 119 of the German Patent Application No. 102 59 935.1 filed Dec. 20, 2002.

The present invention relates to a process for synthesizing nanoparticles, in particular metal salt nanoparticles, and, in particular, to the chemical modification of their surfaces. In this connection, the nanoparticles can also have defined, application-determined properties, for example fluorescent, paramagnetic, optical or other properties, in each case depending on their end use.

Metal salt nanoparticles within the meaning of the present invention exhibit a crystal lattice, or, in the case of doping, a host lattice, whose cation is a metal, in particular a metal of the third subgroup of the periodic system, for example lanthanum, or a metal of the 2nd main group, or a rare earth metal, and whose anion, for example $PO_4^{3-}$, $SO_4^{3-}$ or $VO_4^{3-}$, is obtained from a suitable anion source, for example a free acid of the salts of the nanoparticles which are in each case to be prepared, for example lanthanum phosphate nanoparticles, barium sulfate nanoparticles or sodium vanadate nanoparticles.

These nanoparticles are usually prepared by the formation of nucleation nuclei and subsequent crystalline growth of the particles, usually in the presence of coordinating molecules or ligands. These latter limit the growth of the particles to a size of less than 10 nm, or some 10 s of nm, and have a stabilizing effect on the particles. The synthesis frequently takes place in high-boiling organic solvents, as is disclosed, for example, in international patent application WO 02/20 696, and to which recourse can be had for the purpose of the disclosure of the basic liquid-phase synthesis of nanoparticles. The syntheses of, for example:

- semiconductor quantum dots using trioctylphosphine or trioctylphosphine oxide (TOP/TOPO) (published in: C. B. Murray, D. J. Norris, M. G. Bawendi, J. Am. Chem. Soc. 115, 1993, 8706 ff).
- metal colloids using phosphine and chloride ligands (e.g. $Au_{55}(PPh_3)_{12}C_{16}$) or thiol ligands (e.g. $Au_{64}(SR)_{34}$) (for example published in: G. Schmid, R. Pfeil, R. Boese, F. Bandermann, S. Meyer, G. H. M. Calis, J. W. A. van der Velden, Chem. Ber., 114, 1981, 3534 ff.) and
- doped or undoped inorganic nanoparticles which also exhibit fluorescent and/or magnetic (para-, ferro-, antiferro-, or ferrimagnetic) properties (published in: K. Riwotzki, H. Meyssamy, A. Kornowski, M. Haase; J. Phys. Chem. B 104, 2000, 2824 ff.; WO 02/20695; DE 10111321)

are also regarded as being further examples of this.

However, in many cases, the nanoparticles which are obtained from the abovementioned methods of synthesis are to be able to be used subsequently for particular applications or uses, such as coupling to biologically relevant molecules for medical diagnostics, the preparation of special inks, for example security inks possessing specially selected properties, the preparation of dyes and lacquers, embedding in glass fibers and plastics for communication technology, use as catalyst, or immersion in liquids for the further coating of objects for the purpose of corrosion protection, surface finishing or specially selected surface functionalization.

In this connection, it is usually necessary to disperse the finally synthesized nanoparticles in a new environment which is then typical for this application, for example a special organic matrix or a perfluorinated solvent, or else the nanoparticles are to be used for direct coupling to biologically relevant molecules if they are, for example, to be employed as biolabels.

A disadvantage of the synthesis methods from the abovementioned prior art for such subsequent use of the nanoparticles is the fact that the particles which are synthesized in this way frequently have a strongly hydrophobic character which is caused, for example, by alkyl chains which project outward from the particle surface. The lack of suitable reactive groups gives these particles a relatively inert character. These properties are elicited by the use of coordinating molecules, such as trisethylhexyl phosphate, tributyl phosphate or trioctylphosphine, of which the solvent is directly composed or which are added to a suitable solvent.

These coordinating molecules form an organic sheath around the nanoparticles and also act as a stabilizer against agglomeration. Due to the lack of reactive groups on the outer side of this organic sheath around the nanoparticles, the possibilities of coupling other molecules directly to the particle surface or this sheath are greatly restricted.

However, such a coupling of functional molecules to the particles is usually required for incorporating the nanoparticles into organic matrices, such as polymers or lacquers or other carrier liquids, for the purpose of the abovementioned subsequent uses. Coupling of the nanoparticles to specific biomolecules, such as antibodies, proteins, haptens, nucleic acids, etc., is necessary for the abovementioned use of these particles as biological labels. The use of labels in biological systems for marking or monitoring specific substances has for decades now been an established instrument in medical diagnostics and biotechnological research.

Nanoparticles can, for biological assays, for example, be coupled to a very wide variety of relevant biomolecules and be used, for example, for qualitatively or quantitatively detecting a biological target molecule in a homogeneous, heterogeneous or competitive assay. In this connection, both the coupled-on biomolecules and the target molecules to be detected can, for example, be monoclonal or polyclonal antibodies, proteins, peptides, oligonucleotides, nucleic acids, nucleic acid-like molecules such as peptide nucleic acids (PNAs) or morpholinos, oligosaccharides or polysaccharides, haptens or low molecular weight synthetic or natural antigens.

In order to carry out this incorporation or coupling-on, the particles must be treated appropriately. This includes, where appropriate, the at least partial removal of the coordinating molecules from the particle surface and the coupling-on, which is then to be carried out in a subsequent procedural step, of predetermined reactive groups which are specific in dependence on the intended use. These further procedural steps disadvantageously require additional work input and decrease the yield of nanoparticles which can be effectively applied for the subsequent use. This makes the preparation of nanoparticles which are specifically adapted to the given subsequent use relatively expensive and inefficient.

WO 02/20 696 discloses, as growth control component in liquid-phase synthesis, a variety of organophosphoric compounds which, however, can themselves only carry particular functional groups with regard to the specific control of the growth of the nanoparticles to be synthesized. These substances are therefore selected such that they are able to bind well to the nanoparticle and, on the other hand, prevent further lattice growth. Those which are mentioned by way of example are phosphinic acid esters, phosphonic acid diesters, trialkylphosphanes, and others. Consequently, while this ensures the nanoparticles are synthesized with a narrow size distribution, no contribution is made to simplifying the abovementioned functionalization of the nanoparticles with regard to the subsequent, postsynthetic use of the nanoparticles.

The object of the present invention is therefore to simplify the liquid methods for synthesizing nanoparticles with regard to the subsequent use of the latter.

The parts of the subject matter having the features of the independent claims achieve this object. Advantageous further developments and improvements of the given subject matter of the invention are to be found in the respective subclaims.

The invention proposes adding, to the synthesis mixture, a modifying reagent which binds, by means of a first functional group, to the nanoparticle surface and which carries a second functional group for binding to molecules which are specifically selected in dependence on the subsequent use of the nanoparticles. This consequently dispenses with a postsynthetic, separate, application-specific modification step. The modifying reagent comprises a spacer molecule 14 (FIG. 1) which carries the two functional groups such that they are spaced at a sufficient distance from each other. Examples of the functional groups are carbonyl, carboxyl and amino groups. A new substance class, the pentaalkyl iminobis(methylenephosphono)carboxylates, are particularly suitable for this purpose. The particular achievement of these modifying reagents is, especially, that they permit the nanoparticles to grow in a specifically controlled manner and, at the same time, modify the surface of the growing nanoparticles, (in-situ) during the synthesis, such that the particles can be very readily dissolved in a large number of solvents, resulting in the particles having, immediately after having been synthesized, a certain all-round usability for being dispersed in a variety of solvents, for example in the case of chloroform, toluene, hexane, alcohols, in particular isopropanol, and water. This advantage becomes particularly noticeable in the case of nanoparticles whose surface is, after synthesis, relatively poorly provided with molecules which are themselves suitable for ensuring a useful solubility in appropriate solvents.

A core feature of the invention is that the modifying reagent possesses at least two functional groups, with one being selected such that it is specific for coupling to the nanoparticle and the other being selected such that it is specific for a coupling which is specially designed for the subsequent use of the nanoparticles, with the reagent already being employed during the synthesis of the nanoparticles.

A third functional group 1 (FIG. 2) is optionally present, as an additional coupling site for subsequent applications, on the modifying reagent.

Optionally, and advantageously, the abovementioned new substance class can immediately provide a further (third) functional group, e.g. by way of the ester function, for the application-specific additional coupling.

The present invention is consequently based on the principle that, immediately during their synthesis, the nanoparticles come into contact, at their surfaces, with the modifying reagents, which possess a surface-modifying "external effect". This external effect, which is provided by the invention and which is directed away from the nanoparticle, results in molecules which are typical for the postsynthetic use of the nanoparticles being able to bind on or couple on readily. Coupling sites for the subsequent use in order, for example, to permit ready dispersibility in a particular medium, for example a special solvent, or in order to couple biomolecules to them, are consequently already created during the synthesis. In this connection, the strength of the resulting bond can be specifically selected in accordance with the subsequent use.

Advantageously, some of the modifying reagents additionally at the same time have still another function: by means of their "internal effect" directed toward the nanoparticle, as described in the prior art, they act as a growth control component.

Consequently, according to the invention, suitable reactive groups, for example ester groups and, in particular, carbonyl, carboxyl or amino groups, are already incorporated into the particle surface during the synthesis of the particles as a result of adding the modifying reagents. These specifically selectable reactive groups can then be used for preparing a stable bond, in each case between the nanoparticles and organic matrices (e.g. polymers, lacquers, etc.) or biologically relevant molecules such as proteins, peptides, oligonucleotides or other nucleic acid molecules or nucleic acid-like molecules, such as PNAs or morpholinos, oligosaccharides or polysaccharides, haptens, such as biotin or digoxin, or low molecular weight synthetic or natural antigens or epitopes.

In principle, any inorganic nanoparticles which can be synthesized, in the liquid state, from their starting materials can profit from the present invention.

This applies in a general manner to crystalline, partially crystalline and amorphous nanoparticles. In particular, this applies to nanoparticles whose host material is doped with foreign ions and which are subsequently designated luminescent inorganic doped nanoparticles (lid nanoparticles).

In this connection, the doping can be stoichiometric or nonstoichiometric. This includes, in particular, all materials and material classes which are used as what are termed phosphors in fluorescent screens or fluorescent lamps, as are mentioned, for example, in Ullmann's Encyclopedia of Industrial Chemistry, Wiley-VCH, 6th edition, 2002 Electronic Release, the "Luminescent Materials: 1. Inorganic Phosphors" chapter. In these materials, the foreign ions serve as activators for the emission of fluorescent light following excitation by UV light, visible light or IR light, X-rays, gamma rays or electron beams. In the case of some materials, several types of foreign ion are also incorporated into the host material in order, on the one hand, to produce activators for the emission and, on the other hand, to make the excitation of the particle system more efficient or in order to adapt the absorption wave length, by shifting, to the wave length of a given excitation light source (what are termed sensitizers). The incorporation of several types of foreign ion can also be used for selectively establishing a particular combination of fluorescent bands which are to be emitted by a particle.

The host material of the lid nanoparticles is preferably composed of compounds of the XY type. In this connection, X is a cation from elements of main groups 1a, 2a, 3a or 4a, of the subgroups 2b, 3b, 4b, 5b, 6b or 7b, or of the lanthanides, of the periodic system. In some cases, X can also be a combination or mixture of the abovementioned elements. Y can be a polyatomic anion which contains one or more element(s) of the main groups 3a, 4a or 5a, of the subgroups 3b, 4b, 5b, 6b, 7b and/or 8b, and also elements of the main groups 6a and/or 7a. However, Y can also be a monoatomic anion from the main group 5a, 6a or 7a of the periodic system. The host material of the lid nanoparticles can also consist of an element of the main group 4a of the periodic system. Elements of the main groups 1a or 2a, or from the group containing Al, Cr, Tl, Mn, Ag, Cu, As, Nb, Nd, Ni, Ti, In, Sb, Ga, Si, Pb, Bi, Zn or Co, and/or elements of the lanthanides, can be used as doping. Combinations of two or more of these elements can also be used, in different relative concentrations to each other, as doping material. The concentration of the doping material in the host lattice is between $10^{-5}$ mol % and 50 mol %, preferably between 0.01 mol % and 30 mol %, particularly preferably between 0.1 mol % and 20 mol %.

Preference is given to using sulfides, selenides, sulfoselenides, oxysulfides, borates, aluminates, gallates, silicates, germanates, phosphates, halophosphates, oxides, arsenates, vanadates, niobates, tantalates, sulfates, phosphides, tungstates, molydates, alkali metal halides and other halides, or nitrides, as host materials for the lid nanoparticles. Examples of these material classes, together with the corresponding dopings, are specified in the following list (materials of the type B:A in which B=host material and A=doping material):

LiI:Eu, NaI:Tl; CsI:Tl; CsI:Na; LiF:Mg; LiF:Mg,Ti; LiF:Mg,Na; $KMgF_3$:Mn; $Al_2O_3$:Eu; BaFCl:Eu; BaFCl:Sm; BaFBr:Eu; $BaFCl_{0.5}Br_{0.5}$:Sm; $BaY_2F_8$:A (A=Pr, Tm, Er, Ce); $BaSi_2O_5$:Pb; $BaMg_2Al_{16}O_{27}$:Eu; $BaMgAl_{14}O_{23}$:Eu; $BaMgAl_{10}O_{17}$:Eu; $BaMgAl_2O_3$:Eu; $Ba_2P_2O_7$:Ti; $(Ba,Zn,Mg)_3Si_2O_7$:Pb; $Ce(Mg,Ba)Al_{11}O_{19}$; $Ce_{0.65}Tb_{0.35}MgAl_{11}O_{19}$:Ce,Tb; $MgAl_{11}O_{19}$:Ce,Tb; $MgF_2$:Mn; MgS:Eu; MgS:Ce; MgS:Sm; MgS:(Sm,Ce); (Mg,Ca)S:Eu; $MgSiO_3$:Mn; $3.5MgO.0.5MgF_2.GeO_2$:Mn; $MgWO_4$:Sm; $MgWO_4$:Pb; $6MgO.As_2O_5$:Mn; $(Zn,Mg)F_2$:Mn; $(Zn_4Be)SO_4$:Mn; $Zn_2SiO_4$:Mn; $Zn_2SiO_4$:Mn,As; ZnO:Zn; ZnO:Zn,Si,Ga; $Zn_3(PO_4)_2$:Mn; ZnS:A (A=Ag, Al, Cu); (Zn,Cd)S:A (A=Cu, Al, Ag, Ni); $CdBO_4$:Mn; $CaF_2$:Mn; $CaF_2$:Dy; CaS:A (A=lanthanides, Bi); (Ca,Sr)S:Bi; $CaWO_4$:Pb; $CaWO_4$:Sm; $CaSO_4$:A (A=Mn, lanthanides); $3CA_3(PO_4)_2$.$Ca(F,Cl)_2$:Sb,Mn; $CaSiO_3$:Mn,Pb; $Ca_2Al_2Si_2O_7$:Ce; $(Ca,Mg)SiO_3$:Ce; $(Ca,Mg)SiO_3$:Ti; $2SrO.6(B_2O_3).SrF_2$:Eu; $3Sr_3(PO_4)_2.CaCl_2$:Eu; $A_3(PO_4)_2.ACl_2$:Eu (A=Sr, Ca, Ba); $(Sr,Mr)_2P_2O_7$:Eu; $(Sr,Mg)_3(PO_4)_2$:Sn; SrS:Ce; SrS:Sm,Ce; SrS:Sm; SrS:Eu; SrS:Eu,Sm; SrS:Cu,Ag; $Sr_2P_2O_7$:Sn; $Sr_2P_2O_7$:Eu; $Sr_4Al_{14}O_{25}$:Eu; $SrGa_2S_4$:A (A=lanthanides, Pb); $SrGa_2S_4$:Pb; $Sr_3Gd_2Si_6O_{18}$:Pb,Mn; $YF_3$:Yb,Er; $YF_3$:Ln (Ln=lanthanides); $YLiF_4$:Ln (Ln=lanthanides); $Y_3Al_5O_{12}$:Ln (Ln=lanthanides); $YAl_3(BO_4)_3$:Nd,Yb; $(Y,Ga)BO_3$:Eu; $(Y,Gd)BO_3$:Eu; $Y_2Al_3Ga_2O_{12}$:Tb; $Y_2SiO_5$:Ln (Ln=lanthanides); $Y_2O_3$:Ln (Ln=lanthanides); $Y_2O_2S$:Ln (Ln=lanthanides); $YVO_4$:A (A=lanthanides, In); $Y(P,V)O_4$:Eu; $YTaO_4$:Nb; $YAlO_3$:A (A=Pr, Tm, Er, Ce); YOCl:Yb,Er; $LnPO_4$:Ce,Tb (Ln=lanthanides or mixtures of lanthanides); $LuVO_4$:Eu; $GdVO_4$:Eu; $Gd_2O_2S$:Tb; $GdMgB_5O_{10}$:Ce,Tb; LaOBr:Tb; $La_2O_2S$:Tb; $LaF_3$:Nd,Ce; $BaYb_2F_8$:Eu; $NaYF_4$:Yb,Er; $NaGdF_4$:Yb,Er; $NaLaF_4$:Yb,Er; $LaF_3$:Yb,Er,Tm; $BaYF_5$:Yb,Er; $Ga_2O_3$:Dy; GaN:A (A=Pr, Eu, Er, Tm); $Bi_4Ge_3O_{12}$; $LiNbO_3$:Nd,Yb; $LiNbO_3$:Er; $LiCaAlF_6$:Ce; $LiSrAlF_6$:Ce; $LiLuF_4$:A (A=Pr, Tm, Er, Ce); $Li_2B_4O_7$:Mn, $SiO_x$:Er,Al ($0 \leq x \leq 2$).

Particular preference is given to using the following materials: $YVO_4$:Eu, $YVO_4$:Sm, $YVO_4$:Dy, $LaPO_4$:Eu, $LaPO_4$:Ce, $LaPO_4$:Ce,Tb, $CePO_4$:Tb; ZnS:Tb, $ZnS:TbF_3$, ZnS:Eu, $ZnS:EuF_3$, $Y_2O_3$:Eu, $Y_2O_2S$:Eu, $Y_2SiO_5$:Eu, $SiO_2$:Dy, $SiO_2$:Al, $Y_2O_3$:Tb, CdS:Mn, ZnS:Tb, ZnS:Ag, ZnS:Cu. The particularly preferred materials whose host lattice possesses a cubic lattice structure are selected, in particular, since the number of individual fluorescent bands becomes minimal in the case of these materials. Examples of these materials are: $MgF_2$:Mn; ZnS:Mn, ZnS:Ag, ZnS:Cu, $CaSiO_3$:Ln, CaS:Ln, CaO:Ln, ZnS:Ln, $Y_2O_3$:Ln or $MgF_2$:Ln (Ln=lanthanides).

The present invention can likewise be preferably employed for nanoparticles composed of the following substances, all of which can also, in addition, be doped with one or more elements of the lanthanides and/or Mn, Ag, Cu, Bi, Cr, Sn or Sb.

1. From the halide group: for example $XY_2$ (X=Mg, Ca, Sr, Ba; Y=F, Cl, I), $CaF_2$:Eu(II), $BaF_2$:Eu; $BaMgF_4$:Eu; $LiBaF_3$:Eu; $SrF_2$:Eu; $SrBaF_2$Eu; $CaBr_2$:Eu—$SiO_2$; $CaCl_2$Eu; $CaCl_2$:Eu—$SiO_2$; $CaCl_2$:Eu,Mn—$SiO_2$; $CaI_2$:Eu; $CaI_2$Eu,Mn; $KMgF_3$:Eu; $SrF_2$:Eu(II), $BaF_2$:Eu(II), $YF_3$, $NaYF_4$, 2. From the alkaline earth metal sulfate group: for example $XSO_4$ (X=Mg, Ca, Sr, Ba), $SrSO_4$:Eu, $SrSO_4$:Eu,Mn, $BaSO_4$:Eu, $BaSO_4$:Eu,Mn, $CaSO_4$, $CaSO_4$:Eu, $CaSO_4$:Eu,Mn, and also in each case mixed alkaline earth metal sulfates, including those in combination with magnesium, e.g. $Ca,MgSO_4$:Eu,Mn, 3. From the phosphate and halophosphate group: for example $CaPO_4$:Ce,Mn, $Ca_5(PO_4)_3Cl$:Ce,Mn, $Ca_5(PO_4)_3F$:Ce,Mn, $SrPO_4$:Ce,Mn, $Sr_5(PO_4)_3Cl$:Ce,Mn, $Sr_5(PO_4)_3F$:Ce,Mn, this also codoped with Eu(II) and Eu.Mn, $\alpha$-$Ca_3(PO_4)_2$:Eu; $\beta$-$Ca_3(PO_4)_2$:Eu,Mn; $Ca_5(PO_4)_3Cl$:Eu; $Sr_5(PO_4)_3Cl$:Eu; $Ba_{10}(PO_4)_6Cl_2$:Eu; $Ba_{10}(PO_4)_6Cl_2$:Eu, Mn, $Ca_2Ba_2(PO_4)_3Cl$:Eu; $Ca_5(PO_4)_3F$:$Eu^{2+}X^{3+}$; $Sr_5(PO_4)_3F$:$Eu^{2+}X^{3+}$(X×Nd, Er, Ho, Tb); $Ba_5(PO_4)_3Cl$:Eu; $\beta$-$Ca_3(PO_4)_2$:Eu; $CaB_2P_2O_9$:Eu; $CaB_2P_2O_9$:Eu; $Ca_2P_2O_7$:Eu; $Ca_2P_2O_7$:Eu,Mn; $Sr_{10}(PO_4)_6Cl_2$:Eu; (Sr, Ca, Ba, Mg)$_{10}$(PO$_4$)$_6$Cl$_2$:Eu; $LaPO_4$:Ce; $CePO_4$, 4. From the borate group: for example $LaBO_3$; $LaBO_3$:Ce; $ScBO_3$:Ce $YAlBO_3$:Ce; $YBO_3$:Ce; $Ca_2B_5O_9Cl$:Eu; $xEuOyNa_2O.zB_2O_3$ 5. From the vanadate group: for example $YVO_4$, $YVO_4$:Eu, $YVO_4$:Dy, $YVO_4$:Sm, $YVO_4$:Bi, $YVO_4$:Bi,Eu, $YVO_4$:Bi,Dy, $YVO_4$:Bi,Sm, $YVO_4$:Tm, $YVO_4$:Bi,Tm, $GdVO_4$, $GdVO_4$:Eu, $GdVO_4$:Dy, $GdVO_4$:Sm, $GdVO_4$:Bi; $GdVO_4$:Bi,Eu, $GdVO_4$:Bi,Dy, $GdVO_4$:Bi,Sm 6. From the aluminate group: for example $MgAl_2O_4$:Eu; $CaAl_2O_4$:Eu; $SrAl_2O_4$:Eu; $BaAl_2O_4$:Eu; $LaMgAl_{11}O_{19}$:Eu; $BaMgAl_{10}O_{17}$:Eu; $BaMgAl_{10}O_{17}$:Eu;Mn; $CaAl_{12}O_{19}$:Eu; $SrAl_{12}O_{19}$:Eu; $SrMgAl_{10}O_{17}$:Eu; $Ba(Al_2O_3)_6$:Eu; $(Ba,Sr)MgAl_{10}O_{17}$:Eu, Mn; $CaAl_2O_4$:Eu, Nd; $SrAl_2O_4$:Eu, Dy; $Sr_4Al_{14}O_{25}$:Eu,Dy.

7. From the silicate group: for example $BaSrMgSi_2O_7$:Eu; $Ba_2MgSiO_7$:Eu; $BaMg_2Si_2O_7$:Eu; $CaMgSi_2O_6$:Eu; $SrBaSiO_4$:Eu; $Sr_2Si_3O_8.SrCl_2$:Eu; $Ba_5SiO_4Br_6$:Eu; $Ba_5SiO_4Cl_6$:Eu; $Ca_2MgSi_2O_7$:Eu; $CaAl_2Si_2O_8$:Eu; $Ca_{1.5}Sr_{0.5}MgSi_2O_7$:Eu; $(Ca,Sr)_2MgSi_2O_7$:Eu, $Sr_2LiSiO_4F$:Eu.

8. From the tungstate and molybdate group: for example $X_xWO_6$ (X×Mg, Ca, Sr, Ba), $X_2WO_4$ (X×Li, Na, K, Rb, Cs), $XMoO_4$ (X×Mg, Ca, Sr, Ba) and also polymolybdates or polytungstates and/or the salts of the corresponding hetero- or isopoly acids.

9. From the germanate group: for example $Zn_2GeO_4$

10. From the following group: $ALnO_2$:Yb, Er (A=Li, Na; Ln=Gd, Y, Lu); $Ln_2O_3$:Yb, Er (Ln=La, Gd, Y, Lu); $LnAO_4$:Yb, Er (Ln=La, Y; A=P, V, As, Nb); $Ca_3Al_2Ge_3O_{12}$:Er; $Gd_2O_2S$:Yb, Er; $La_2S$:Yb,Er.

The present invention can also be used for synthesizing oxidic nanoparticles which are prepared by way of precipitation reaction, for example $CeO_2$, $Y_2O_3$, ZnO, $SnO_2$, $TiO_2$, etc.

While the present invention can preferably be used for synthesizing crystalline host lattices of the previously described compounds, it does not exclude the synthesis of amorphous or partially crystalline forms of the particles.

Nanoparticles according to the present invention have a size of from 1 nm to 1 μm, which size can be adjusted selectively using the modifying reagents which are provided in accordance with the invention, and can be prepared in a narrow size distribution up to a size of a few nanometers (approximately 2 nanometers).

The modification, according to the invention, of the surface is effected during the formation of the nanoparticles, i.e. is in-situ modification, in contrast to postsynthetic modification. The nanoparticles which are obtained can therefore be synthesized with a desired chemical surface directly in one step.

The crystal growth rates, and the resulting particle diameters, differ in magnitude depending on the type and chemical composition of the host lattice and on synthesis conditions such as solvent and temperature. The size of the particles can be influenced selectively by the time at which the modifying reagent is added to the reaction solution. The time which elapses during the synthesis period before the modifying reagent is added is directly proportional to the planned average size of the nanoparticles.

Lattices which exhibit rapid crystal formation and tend to form large nanoparticles (e.g. 20-30 nm) can have their growth limited by the modifying reagent being added directly to the reaction solution prior to heating whereas, in the case of particle types which tend toward small diameters, a time-delayed addition allows crystal growth to make initial progress.

It is consequently possible, by choosing the time at which the modifying reagent is added, in accordance with the invention, to the synthesis mixture, to control particle growth and thereby obtain desired particle sizes in addition to a chemically modified surface.

The modification of the surface, that is the selective attachment of chemical groups, makes it possible to alter the properties of the nanoparticles with regard to their solubility in organic and inorganic solvents of widely differing polarity. Incorporation into plastics, lacquers, inks and polymers, and homogeneous distribution in these matrices, can also be achieved by means of appropriate modification. Furthermore, coupling to other molecules, such as biomolecules, can also be effected by attaching functional groups. This then makes it possible to use the fluorescent or magnetic properties of the nanoparticles as labels for biological applications.

Furthermore, modifying with chemical compounds which carry two or more functional groups can introduce the possibility of analytically detecting the surface modification, for example by means of the carbonyl oscillation of a carbonyl function, which oscillation can be sensitively detected by means of IR spectroscopy.

According to the invention, the following compounds can be used as modifying reagents:
compounds having one or more phosphonic acid/ester groups (mono- or oligophosphonic acids; mono- or oligophosphonic acid esters);
iminobisphosphonic acids/esters;
amines, primary and secondary;
alcohols;
boronic acids/esters;
alkyl halides;
organic phosphates/borates;
thiols, disulfides and polysulfides;
sulfonates;
and also bifunctional compounds having one functionality, corresponding to one of the abovementioned functionalities, which is located at one end of a hydrocarbon chain of variable length, e.g. $C_6$ or $C_{11}$, and having another functional group which is located at the other end of this hydrocarbon chain and which can, for example, be a carbonyl function which is available for further chemical reactions, e.g. esterifications, amidation, etc.

However, particularly suitable modifying reagents are constituted by a new substance class, the pentaalkyl iminobis(methylenephosphono)carboxylates of the formula I

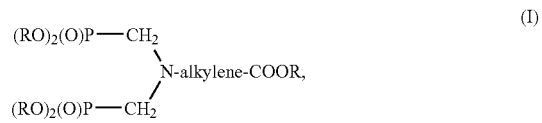

where
R is a $C_1$-$C_4$-alkyl radical and
alkylene is a $C_1$-$C_{22}$-alkylene radical or $C_7$-$C_{20}$-alkylenearylene radical, preferably a $C_5$-$C_{17}$-alkylene radical, which can be linear or branched and can, in addition, carry, as additional substituents, halogen atoms, COOR groups, alkoxy groups, bis(dialkoxyphosphorylmethyl) amino groups or aryl radicals.

In this case, the phosphate groups couple to the surface, and in the above sense are directed inward, and the carboxylic acid or ester functions are directed outward.

The following is a route for preparing the abovementioned new substance class:
a process for preparing, in accordance with the invention, the pentalkyl iminobis(methylenephosphono)carboxylates, wherein compounds of the formula II

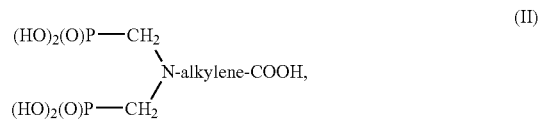

where alkylene has the abovementioned meaning, are reacted with orthoesters of the formula III $(RO)_3C$—X  (III), where
R has the meaning given above with regard to formula (I), and
X is a hydrogen atom, a $C_1$-$C_4$-alkyl radical or a phenyl radical, preferably hydrogen,
at temperatures of 60-200° C.

Compounds of the formula II can be obtained by reacting amino acids with 2-3 moles of formaldehyde and 2-3 moles of phosphorous acid, based on the amino group.

The following amino acids can be used in this reaction: glycine, alanine, leucine, glutamic acid, aspartic acid, lysine, valine, phenylalanine, beta-alanine, 4-aminobutyric acid, 6-aminocaproic acid, 11-aminoundecanoic acid, 7-aminoheptanoic acid, 8-aminooctanoic acid, 12-aminododecanoic acid and 4-aminomethylbenzoic acid, preferably 11-aminoundecanoic acid and 6-aminocaproic acid.

The compounds of the formula III which can be used are the trimethyl, triethyl, tripropyl, triisopropyl and tributyl esters of orthoformic acid, orthoacetic acid and orthobenzoic acid, preferably orthoformic acid.

The reaction takes place at from 60° C. to 200° C. In a preferred embodiment, trialkyl orthoformates are used at their boiling temperature. The reaction takes place in the presence or absence, preferably in the absence, of solvents. At least two moles of orthoester are used for each phosphoryl group in the starting compound while at least one mole of orthoester is used for each carboxyl group. After the reaction, unreacted starting compounds are filtered off and the excess of orthoester is distilled off. While the pentaalkyl iminobis(methylenephosphono)carboxylates according to the invention can usually not be purified by vacuum distillation, they accrue at a purity which is adequate for the planned use. They can be purified by chromatographic methods.

The pentaalkyl iminobis(methylenephosphono)carboxylates according to the invention can advantageously be used as modifying solvent for preparing nanoparticulate metal salts with, for example, a metal halide being reacted with an acid, e.g. phosphoric acid or boric acid. The nanoparticles are characterized by a small particle size and by specific surface functionalization with ester groups. The average diameters of the nanoparticles are from 1 to 100 nm.

Furthermore, according to a special, advantageous aspect of the present invention, 10 the following compounds of the formula IV can be used as solvents for preparing metal salt nanoparticles:

$$(RO)_2(O)P-CH_2 \atop (RO)_2(O)P-CH_2 \Big\rangle N-Alk, \quad (IV)$$

where

R has the meaning given above with regard to formula (I), and

Alk is a $C_4$-$C_{22}$-alkyl radical or $C_7$-$C_{30}$ aralkyl or arylalkyl radical.

These compounds of the formula IV, which are known per se, can be obtained by heating compounds of the formula V $$(HO)_2(O)P-CH_2 \atop (HO)_2(O)P-CH_2 \Big\rangle N-Alk, \quad (V)$$

where

Alk has the meaning given above with regard to formula (IV), with compounds of the formula (III).

The compounds of the formula V can be obtained by reacting the $H_2N$-Alk amines with phosphorous acid and formaldehyde.

Selecting a pentaalkyl iminobis(methylenephosphono) carboxylate as modifying reagent results in the additional advantage that the nanoparticles possess particularly good solution properties and the growth in size of the particles can be controlled in a particularly reliable manner. As well as this, the abovementioned additional, third functional group, e.g. as ester group, is available for further coupling depending on the intended application.

A further advantage is that a carbonyl group which is present in the modifying reagent can be reliably detected by means of IR spectroscopy, thereby making it readily possible to detect the fact that the desired surface modification of the nanoparticles has indeed taken place.

Particular preference is given to pentaethyl iminobis (methylenephosphono)-undecanoate and pentaethyl iminobis(methylenephosphono)caproate.

The two substances couple well to the surfaces of the nanoparticles and are soluble in the solvents employed, as are described below. Homologs possessing similar chain lengths exhibit similarly good properties.

As is evident from the above summary and from the preparation and application examples which follow, the teaching according to the invention can be used to synthesize a wide variety of nanoparticles specifically for subsequent intended uses, with both the range of nanoparticles and the range of the application-specific molecules to which the nanoparticles are able to couple being very diverse.

Exemplary embodiments of the invention are depicted in the drawings and explained in more detail in the subsequent description.

Figure 2:
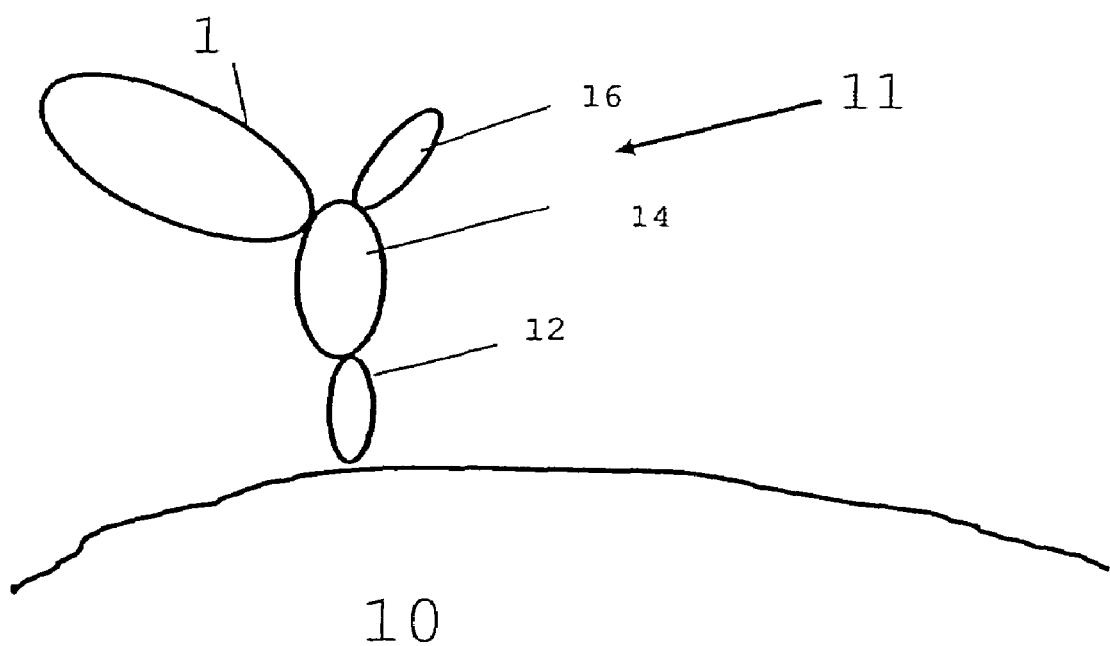

FIG. 1 shows a diagram for the purpose of depicting a modifying reagent, which is provided in accordance with the invention and which possesses two functional groups, on a nanoparticle surface, and FIG. 2 shows a depiction in accordance with FIG. 1 with the reagent carrying three functional groups.

The surface of a nanoparticle 10 is depicted diagrammatically as a line, without individual molecules being shown, in the lower part of FIG. 1. In this figure, the modifying reagent 11, which is employed in accordance with the invention, is shown diagrammatically taking a single molecule as an example. This molecule contains three essential components: a spacer or carrier 14 which carries two functional groups 12 and 16. The functional group 12 couples to the nanoparticle surface and the functional group 16 projects away from the surface of the nanoparticle. This group is available for an application-specific coupling to other molecules, as has already been mentioned above. In general, the spacer 14 is required so as to ensure that the functional groups do not mutually restrict the way in which they operate or entirely neutralize each other. The two functional groups can be linked to each other by at least one $CH_2$ group (or another bridging atom).

In the example shown in FIG. 1, the components which are mentioned, i.e. 10, 12, 14 and 16, can, for example, consist of the following chemical substances:

10: nanoparticle surface possessing phosphate groups —P(=O)(—OH)$_2$

12: diethyl phosphonate —P(=O)(—OCH$_2$CH$_3$)$_2$

14: alkyl chain (CH$_2$)$_x$, X=1-?

16: ethyl carboxylate —C(=O)O—CH$_2$CH$_3$.

According to the invention, this thereby achieves a coupling of the phosphonic acid ester to the surface phosphate groups with the formation of diphosphonate grouping —P(=O)(—OR)—P(=O)(—OR)— (transesterification). Alternatively, the phosphate group can be incorporated into the nanoparticle surface. The free carboxylic acid ester function is available for subsequent reactions.

In FIG. 2, the components of which can be formed as described in FIG. 1, a further, the third, functional group 18 is now available in addition to the configuration shown in FIG. 1, as has already been mentioned above.

EXAMPLES OF PREPARING MODIFYING REAGENTS

Examples of preparing some pentaalkyl iminobis(methylenephosphono)carboxylates are first of all given below:

Example 1

Preparing iminobis(methylenephosphono)undecanoic acid 200 g of 11-aminoundecanoic acid, 170 g of phosphorous acid, 200 ml of water and 200 ml of concentrated hydrochloric acid are mixed and heated to 100° C. and 324 g of formalin (37%) are added within the space of 1 h. The mixture is stirred at 100° C. for a further 1 h and then allowed to cool down to room temperature; the precipitated product is then filtered off with suction. 460 g of product are obtained.

Example 2

Preparing iminobis(methylenephosphono)caproic acid 131 g of 6-aminocaproic acid, 170 g of phosphorous acid, 200 ml of water and 200 ml of concentrated hydrochloric acid are mixed and heated to 100° C. and 324 g of formalin (37%) are then added within the space of 1 h. The mixture is stirred at 100° C. for a further 1 h and the water is then distilled off in vacuo. 240 g of product are obtained.

Example 3

Preparing pentaethyl iminobis(methylenephosphono)undecanoate 100 g of the product from example 1 are heated at reflux for 14 h with 1000 g of triethyl orthoformate. The unreacted starting material is filtered off and all the constituents which are volatile up to 140° C. at 5 Torr are distilled off. 65 g of product (characterized by $^1$H NMR spectroscopy) are obtained.

Example 4

Preparing pentaethyl iminobis(methylenephosphono)caproate 200 g of the product from example 2 are heated, at reflux for 13.5 h, with 2000 g of triethyl orthoformate. The unreacted starting material is filtered off and all the constituents which are volatile at up to 140° C. at 5 Torr are distilled off. 148 g of product (characterized by $^1$N NMR spectroscopy) are obtained.

Example 5

Preparing pentaisopropyl iminobis(methylenephosphono)undecanoate

The procedure is as given in example 3, with 1000 g of triisopropyl orthoformate being used as the ortho ester. 163 g of product (characterized by $^1$N NMR spectroscopy) are obtained.

PREPARATION EXAMPLES FOR SYNTHESIZING MODIFIED NANOPARTICLES

1st Example

A description of a preferred embodiment of a preparation process according to the invention for preparing LaPO$_4$:Ce, Tb nanoparticles which are modified with phosphonic acids, which are envisaged in accordance with the invention, is given below by way of example:

The salts LaCl$_3$ 7H$_2$O (2.4 mmol), CeCl$_3$ 7H$_2$O (2.7 mmol) and TbCl$_3$ (0.9 mmol) are dissolved in methanol (approx. 2.5 ml), in a 50 ml-capacity main flask provided with a jacketed coil condenser, a temperature sensor and a plugged-in heating mantle, and tris-2-ethylhexyl phosphate (TEHP) is then added to the solution. Methanol and water of crystallization are initially removed at room temperature (1-2 h) and then at 50° C. in vacuo over a period of several hours.

Dry orthophosphoric acid (6 mmol) is dissolved in tetra-ethylene glycol dimethyl ether (1.4 ml) in a second flask.

The phosphonic acid 11-phosphonoundecanoic acid (1.2 mmol) is dissolved in TEHP (3-4 ml) in a third flask, with it being possible to warm the mixture where appropriate.

The salt solution is diluted with TEHP (4 ml) at 50° C. and under a nitrogen atmosphere, after which trioctylamine (8.0 ml, 18.0 mmol), the phosphoric acid solution and the phosphonic acid solution are added. The reaction mixture is then heated at 200° C. for 15-18 h. After it has cooled down, it is then poured onto methanol (150 ml) in order to precipitate the nanoparticles. The precipitate which has sedimented out is decanted and then centrifuged. After having been washed with methanol, it is dried in vacuo.

2nd Example

A description of a preferred embodiment of a preparation process according to the invention for preparing LaPO$_4$:Ce, Tb nanoparticles which are modified with liquid phosphonic acid esters, which are envisaged in accordance with the invention, is given below by way of example:

The salts LaCl$_3$ 7H$_2$O (2.4 mmol), CeCl$_3$ 7H$_2$O (2.7 mmol) and TbCl$_3$ (0.9 mmol) are dissolved in methanol (approx. 2.5 ml), in a 50 ml-capacity main flask provided with a jacketed coil condenser, a temperature sensor and a plugged-in heating mantle, and tris-2-ethylhexyl phosphate (TEHP) is then added to the solution. Methanol and water of crystallization are initially removed at room temperature (1-2 h) and then at 50° C. in vacuo for several hours.

Dry orthophosphoric acid (6 mmol) is dissolved in tetra-ethylene glycol dimethyl ether (1.4 ml) in a second flask.

The phosphonic acid ester triethyl 11-phosphonoundecanoate (1.35 ml) is prepared, in a third vessel, as a 5% solution in TEHP (v/v).

The salt solution is diluted with TEHP (8 ml) at 50° C. and under a nitrogen atmosphere, after which trioctylamine (8.0 ml, 18.0 mmol), the phosphoric acid solution and the phosphonic acid solution are added. The reaction mixture is then heated at 200° C. for 15-18 h. After it has cooled down, it is poured onto methanol (150 ml) in order to precipitate the nanoparticles. The precipitate which has sedimented out is decanted and then centrifuged. After having been washed with methanol, it is dried in vacuo.

3rd Example

A description of a preferred embodiment of a preparation process according to the invention for preparing LaBO$_3$:Ce, Tb nanoparticles which are modified with iminobisphosphonic acid esters, which are envisaged in accordance with the invention, is given below by way of example.

The salts LaCl$_3$ 7H$_2$O (1.2 mmol), CeCl$_3$ 7H$_2$O (1.35 mmol) and TbCl$_3$ (0.45 mmol) are dissolved in methanol (approx. 1.2 ml), in a 50 ml-capacity main flask provided with a jacketed coil condenser, a temperature sensor and a plugged-in heating mantle, and tributyl phosphate (TBP) (27 ml) is then added to the solution. Methanol and water of crystallization are initially removed at room temperature (1-2 h) and then at 50° C. in vacuo over a period of several hours.

Trioctylamine (13.5 mmol) and H$_3$BO$_3$ (4.5 mmol) are then added to the salt solution, at 50° C. and under a nitrogen atmosphere, and the mixture is heated at 200° C. After a reaction period of 4 h, the pentaethyl iminobis(methylenephosphono)caproate (0.275 g, 0.6 mmol) is added to the synthesis mixture and the reaction is continued for a further 15 h. After the reaction mixture has cooled down, it is poured onto methanol (120 ml) in order to precipitate the nanoparticles. The precipitate which has sedimented out is decanted and then centrifuged. After having been washed with methanol, it is dried in vacuo.

4th Example

A description of a preferred embodiment of a preparation process according to the invention for amino functionalizing the $LaPO_4$:Ce,Tb nanoparticles which are described in 2., and which are modified with liquid phosphonic acid esters which are envisaged in accordance with the invention, is given below by way of example:

The nanoparticles (17.5 mg, 50 nmol) prepared in 2. are heated at 150° C., in a round-bottomed flask, with 1,4-bis (3-aminopropoxy)butane (1.02 g, 5 mmol). At approx. 140° C., an optically clear, slightly yellowish dispersion is present. This latter is stirred at 150° C. for a further 3 h and also remains clear after having been cooled down to RT. It is dialyzed overnight against 2×2 L of 10 mM Na carbonate buffer, pH 8.5 (Spectra/Por dialysis tubing, 5-6000 MWCO, spectrum, Netherlands). The dialysate is turbid.

5th Example

A description of a preferred embodiment of a process according to the invention for coupling an antibody directed against amino terminal procollagen type III (PIIINP) to $LaPO_4$:Ce,Tb nanoparticles which have been amino functionalized as described above under 4. is given below by way of example:

The nanoparticles (3 mg, 8.4 nmol) which have been prepared above in the 4th example are transferred to TSE buffer, pH 8.5 (0.04 M NaCl; 0.05 M triethanolmaine-HCl; 0.04 M NaOH; 0.5 mM EDTA; 0.1% Tween 20; pH 8.5). For this, the particles are centrifuged at 3000 g for 3×15 min and the sediment is in each case taken up in 700 µl of TSE buffer, pH 8.5, after the supernatant has been decanted off. In order to activate the particles, they are incubated, at 25° C. for 15 min, with a 40-fold excess (50 µl of a 20 mM solution in water) of sulfo-SIAB (sulfosuccinimidyl(4-iodoacetyl)aminobenzoate, Perbio Science Germany GmbH, Bonn). The reaction is stopped by adding 12 µl of 1M glycine (12-fold excess) and the free sulfo-SIAB is separated off by centrifugation (see above).

The monoclonal antibody 35J23 (TSD, Newark, Del., USA), which is directed against PIIINP (aminoterminal procollagen type III) is activated with a 30-fold molar excess of 2-iminothiolane (2-IT, Traut's reagent, Perbio Science Germany GmbH, Bonn): 10 mg of antibody 35J23 are transferred, using Centricon ultrafiltration tubes (exclusion size 50 kD, Millipore, Schwalbach, Germany) into TSE8 buffer (exchange factor 1000, TSE8: (100 mmol of triethanolamine, 50 mmol of sodium chloride, 1 mmol of EDTA in water, pH 8.5). The protein concentration is adjusted to 7-8 mg/ml. 150 µl of a 10 mM solution of 2-imminothiolane in TSE8 buffer are added to the antibody solution and the mixture is allowed to react for 15 minutes. The antibody, which has been thiol-activated in this way, is rebuffered at 4° C. with TSE8 buffer, as described above, in order to remove activator molecules which have not reacted, and concentrated down to 2 ml. The solutions containing sulfoSIAB-activated nanoparticles and the activated antibody are combined and stirred overnight at room temperature. The dispersion of the amplified detection particles which has thus been obtained is separated off from unreacted antibody by centrifugation as described above.

A description of a preferred embodiment of a process according to the invention for detecting aminoterminal procollagen type III using the $LaPO_4$:Ce,Tb nanoparticles which were coupled with antibody as described above under 5. is given below:

The assay for determining procollagen III in serum samples for diagnostic purposes is a sandwich immunoassay using biotinylated monoclonal trapping antibodies and nanoparticle-coupled monoclonal antibodies for the detection.

Biotinylating the monoclonal antibody Mab P3P 296/2/27 (Dade Behring, Marburg) which is directed against aminoterminal procollagen type III: the antibody is dissolved, to a concentration of 1 mg/ml, in 0.1 M carbonate buffer, pH 8.5, and this solution is incubated, at RT for 4 hrs and while being rotated, with a 20-fold molar excess of biotin-X-NHS (sulfobiotin-aminocaproic acid N-hydroxysuccinimide ester, Calbiochem, Schwalbach), which is dissolved in water. Subsequently, the mixture is dialyzed against PBS buffer (8 mM $K_2HPO_4$; 150 mM NaCl; 2 mM $Na_2HPO_4$; pH 7.4) (Spectra/Por dialysis tubing, 5-6000 MWCO, spectrum, Netherlands).

Immunoassay: 1 µg of the nanoparticle conjugate which is described above under 5. is incubated, at 37° C. for 1 h in PBS buffer containing 0.1% BSA, with 0.65 µg of the biotinylated antibody Mab P3P 296/3/27 in the presence of PIIINP calibrators (from fetal bovine serum, concentrations: 0; 5.2; 9.6; 21; 57 and 151 ng/ml) in a volume of 100 µl; the whole is then added to streptavidin-coated microtiter plates (BD BioCoat streptavidin assay plates, BD GmbH Heidelberg) and incubation at 37° C. is carried out for a further 15 min. After it has been washed 3 times with in each case 200 µl of PBS/0.1% BSA, the microtiter plate is read out in a Tecan SAFIRE Monochromator plate reader (Tecan GmbH, Crailsheim, Germany) using the following settings: excitation wave length: 280 nm (10 nm slit width); scan emission wave lengths of 450-650 nm (10 nm slit width); time delay: 40 µs and time window: 2000 µs. A duplicate determination is carried out in the case of each value. The measured values are plotted in a graph against the calibrator concentrations employed and give a calibration curve which can be used to determine concentrations of PIIINP, which are measured in human serum samples in an analogous manner.

Although the present invention has been described above using preferred exemplary embodiments, it is not restricted to these embodiments but can, on the contrary, be modified in a wide variety of ways.

Finally, the features of the subclaims can, insofar as they are independent of each other, be combined essentially freely with each other and not be combined with each other using the order which exists in the claims.

The invention claimed is:

1. A process for preparing metal salt nanoparticles in a liquid phase reaction, comprising mixing starting materials of the nanoparticles in a synthesis mixture and growing the nanoparticles from said synthesis mixture during a synthesis period, said process further comprising adding a modifying reagent to the synthesis mixture within the synthesis period, with the modifying reagent exhibiting a first functional group for coupling to one of said nanoparticles and a second functional group for binding to a molecule other than said nanoparticles, wherein the modifying reagent is a pentaalkyl iminobis(methylenephosphono)carboxylate of the formula I:

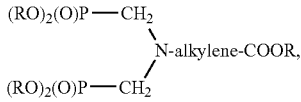
(I)

wherein
R is a $C_1$-$C_4$-alkyl radical; and
alkylene is a $C_1$-$C_{22}$-alkylene radical or $C_7C_{20}$-alkylene-arylene radical, which can be linear or branched and can, in addition, carry, as additional substituents, halogen atoms, COOR groups, alkoxy groups, bis(dialkoxyphosphorylmethyl)amino groups or aryl radicals wherein the starting material comprise cations comprising a metal salt, and anions which are selected from the group consisting of alkaline metal halides, alkaline earth metal sulfates, phosphates, halophosphates, borates, vanadates, aluminates, silicates, tungstates, molybdates and germanates, all of which may be doped with one or more elements of the lanthanides and/or Mn, Ag, Cu, Pb, Bi, Cr, Sn or Sb.

2. The process as claimed in claim 1, wherein host materials of said metal salt nanoparticles are selected from the group consisting of:
a) $XY_2$ (X=Mg, Ca, Sr, Ba; Y=F, Cl, I), $CaF_2$:Eu(II), $BaF_2$:Eu; $BaMgF_4$:Eu; $LiBaF_3$:Eu; $SrF_2$:Eu; $SrBaF_2$Eu; $CaBr_2$:Eu—$SiO_2$; $CaCl_2$Eu; $CaCl_2$:Eu—$SiO_2$; $CaCl_2$:Eu,Mn—$SiO_2$; $CaI_2$:Eu; $CaI_2$Eu,Mn; $KMgF_3$:Eu; $SrF_2$:Eu(II), $BaF_2$:Eu(II), $YF_3$, $NaYF_4$,
b) $XSO_4$ (X=Mg, Ca, Sr, Ba), $SrSO_4$:Eu, $SrSO_4$:Eu,Mn, $BaSO_4$:Eu, $BaSO_4$:Eu,Mn, $CaSO_4$, $CaSO_4$:Eu, $CaSO_4$:Eu,Mn, and also in each case mixed alkaline earth metal sulfates, optionally in combination with magnesium,
c) $CaPO_4$:Ce,Mn, $Ca_5(PO_4)_3Cl$:Ce,Mn, $Ca_5(PO_4)_3F$:Ce,Mn, $SrPO_4$:Ce,Mn, $Sr_5(PO_4)_3Cl$:Ce,Mn, $Sr_5(PO_4)_3F$:Ce,Mn, this also codoped with Eu(II) and Eu,Mn, $\alpha$-$Ca_3(PO_4)_2$:Eu; $\beta$-$Ca_3(PO_4)_2$:Eu,Mn; $Ca_5(PO_4)_3Cl$:Eu; $Sr_5(PO_4)_3Cl$:Eu; $Ba_{10}(PO_4)_6Cl$:Eu; $Ba_{10}(PO_4)_6Cl$:Eu,Mn, $Ca_2Ba_3(PO_4)_3Cl$:Eu; $Ca_5(PO_4)_3F$:$Eu^{2+}X^{3+}$; $Sr_5(PO_4)_3F$:$Eu^{2+}X^{3+}$(X=Nd, Er, Ho, Tb); $Ba_5(PO_4)_3Cl$:Eu; $\beta$-$Ca_3(PO_4)_2$:Eu; $CaB_2P_2O_9$:Eu; $CaB_2P_2O_9$:Eu; $Ca_2P_2O_7$:Eu; $Ca_2P_2O_7$:Eu,Mn; $Sr_{10}(PO_4)_6Cl_2$:Eu; (Sr, Ca, Ba, Mg)$_{10}$(PO$_4$)$_6$Cl$_2$:Eu; $LaPO_4$:Ce; $CePO_4$,
d) $LaBO_3$; $LaBO_3$:Ce; $ScBO_3$:Ce $YAlBO_3$:Ce; $YBO_3$:Ce; $Ca_2B_5O_9Cl$:Eu; $xEuOyNa_2OzB_2O_3$,
e) $YVO_4$, $YVO_4$:Eu, $YVO_4$:Dy, $YVO_4$:Sm, $YVO_4$:Bi; $YVO_4$:Bi,Eu, $YVO_4$:Bi,Dy, $YVO_4$:Bi,Sm, $YVO_4$:Tm, $YVO_4$:Bi,Tm, $GdVO_4$, $GdVO_4$:Eu, $GdVO_4$:Dy, $GdVO_4$:Sm, $GdVO_4$:Bi; $GdVO_4$:Bi,Eu, $GdVO_4$:Bi,Dy, $GdVO_4$:Bi,Sm,
f) $MgAl_2O_4$:Eu; $CaAl_2O_4$:Eu; $SrAl_2O_4$:Eu; $BaAl_2O_4$:Eu; $LaMgAl_{11}O_{19}$:Eu; $BaMgAl_{10}O_{17}$:Eu; $BaMgAl_{10}O_{17}$:Eu, Mn; $CaAl_{12}O_{19}$:Eu; $SrAl_{12}O_{19}$:Eu; $SrMgAl_{10}O_{17}$:Eu; $Ba(Al_2O_3)_6$:Eu; $(Ba,Sr)MgAl_{10}O_{17}$:Eu, Mn; $CaAl_2O_4$:Eu,Nd; $SrAl_2O_4$:Eu, Dy: $Sr_4Al_{14}O_{25}$:Eu,Dy,
g) $BaSrMgSi_2O_7$:Eu; $Ba_2MgSiO_7$:Eu; $BaMg_2Si_2O_7$:Eu; $CaMgSi_2O_6$:Eu; $SrBaSiO_4$:Eu; $Sr_2Si_3O_8.SrCl_2$:Eu; $Ba_5SiO_4Br_6$:Eu; $Ba_5SiO_4Cl_6$:Eu; $Ca_2MgSi_2O_7$:Eu;

$CaAl_2Si_2O_8$:Eu; $Ca_{1.5}Sr_{0.5}MgSi_2O_7$:Eu; $(Ca,Sr)_2MgSi_2O_7$:Eu, $Sr_2LiSiO_4F$:Eu,
h) $X_3WO_6$ (X=Mg, Ca, Sr, Ba), $X_2WO_4$ (X=Li, Na, K, Rb, Cs), $XMoO_4$ (X=Mg, Ca, Sr, Ba) and also polymolybdates or polytungstates and/or the salts of the corresponding hetero- or isopoly acids,
i) $Zn_2GeO_4$,
j) the following compounds: $ALnO_2$:Yb, Er (A=Li, Na; Ln=Gd, Y, Lu); $Ln_2O_3$:Yb, Er (Ln=La, Gd, Y, Lu); $LnAO_4$:Yb, Er (Ln=La, Y; A=P, V, As, Nb); $Ca_3Al_2Ge_3O_{12}$:Er; $Gd_2O_2S$:Yb, Er; $La_2S$:Yb,Er,
all of which may be doped with one or more elements of the lanthanides and/or Mn, Ag, Cu, Pb, Bi, Cr, Sn or Sb within host lattice.

3. The process as claimed in claim 1, wherein doping elements are present in a host lattice at a concentration between $10_{-5}$ mol % and 50 mol %.

4. The process as claimed in claim 1, wherein the modifying reagent is a pentaethyl iminobis(methylenephosphono)undecanoate or a pentaisopropyl iminobis(methylenephosphono)undecanoate.

5. The process as claimed in claim 1, wherein the modifying reagent is a pentaethyl iminobis(methylenephosphono)caproate or pentaisopropyl iminobis(methylenephosphono)caproate.

6. The process as claimed in claim 1, wherein the time which elapses during the synthesis period before the modifying reagent is added is directly proportional to a planned average size of the nanoparticles.

7. The process as claimed in claim 1, wherein the synthesis mixture comprises compounds of the formula IV as solvent:

(IV)

where
R has the meaning given above with regard to formula (I), and
Alk is a $C_4$-$C_{22}$-alkyl radical or $C_7$-$C_{30}$ aralkyl or aralkyl radical.

8. Method of using the nanoparticles which are prepared as claimed in claim 1, comprising coupling the nanoparticles to biologically relevant molecules for the purpose of marking them.

9. Method of using the nanoparticles which are prepared as claimed in claim 1 for a subsequent intended application, comprising coupling the nanoparticles to application-specific molecules, with the coupling being selectively promoted or made possible by means of one of the functional properties of the modifying reagent.

10. The process as claimed in claim 1, wherein doping elements are present in a host lattice at a concentration between 0.01 mol % and 30 mol %.

11. The process as claimed in claim 1, wherein doping elements are present in a host lattice at a concentration between 0.1 mol % and 20 mol %.

* * * * *